United States Patent
Hendriksen et al.

(10) Patent No.: US 8,845,710 B2
(45) Date of Patent: Sep. 30, 2014

(54) METHOD AND APPARATUS FOR INTRODUCING INTRALUMINAL PROSTHESES

(75) Inventors: Per Hendriksen, Herlufmagle (DK); Jacob Lund Clausen, Kgs. Lyngby (DK)

(73) Assignee: Cook Medical Technologies LLC, Bloomington, IN (US)

( * ) Notice: Subject to any disclaimer, the term of this patent is extended or adjusted under 35 U.S.C. 154(b) by 970 days.

(21) Appl. No.: 12/070,869

(22) Filed: Feb. 21, 2008

(65) Prior Publication Data

US 2009/0143738 A1    Jun. 4, 2009

Related U.S. Application Data

(60) Provisional application No. 61/004,804, filed on Nov. 30, 2007.

(51) Int. Cl.
*A61M 25/09* (2006.01)
*A61F 2/95* (2013.01)
*A61F 2/01* (2006.01)

(52) U.S. Cl.
CPC ............ *A61F 2/95* (2013.01); *A61F 2002/9517* (2013.01); *A61F 2002/011* (2013.01)
USPC ....................................................... 623/1.11

(58) Field of Classification Search
CPC .................. A61F 2002/011; A61F 2002/9517; A61F 2/95; A61F 2/966; A61F 2/0095; A61F 2/962
USPC ........ 623/1.11, 1.12; 606/108, 192, 194, 200; 604/164.12, 165.01
See application file for complete search history.

(56) References Cited

U.S. PATENT DOCUMENTS

| | | | | |
|---|---|---|---|---|
| 5,026,377 A | * | 6/1991 | Burton et al. | 606/108 |
| 5,201,757 A | * | 4/1993 | Heyn et al. | 606/198 |
| 5,910,144 A | * | 6/1999 | Hayashi | 606/108 |
| 6,152,947 A | | 11/2000 | Ambrisco et al. | |
| 6,319,268 B1 | | 11/2001 | Ambrisco et al. | |
| 6,991,646 B2 | * | 1/2006 | Clerc et al. | 623/1.11 |
| 2001/0012944 A1 | * | 8/2001 | Bicek et al. | 606/108 |
| 2003/0171770 A1 | | 9/2003 | Kusleika et al. | |
| 2005/0090887 A1 | | 4/2005 | Pryor | |

(Continued)

FOREIGN PATENT DOCUMENTS

GB            2200848 A     8/1988
WO      WO 02/11627 A2     2/2002

(Continued)

*Primary Examiner* — Thomas McEvoy
*Assistant Examiner* — Julie A Szpira
(74) *Attorney, Agent, or Firm* — Brinks Gilson & Lione

(57) ABSTRACT

An introducer for use in the implantation and retrieval of a device in a patient includes a catheter (43) within which a stylet (14) is slidably carried, the stylet (14) being biased to a retracted position by a spring (35) and deployable by depression of an actuator (50). A locking device (40) locks the stylet (14) relative to the catheter (43) such that the locking device (40) must be disengaged prior to operation of the actuator (50). In the preferred embodiment, both the locking device (40) and the actuator (50) must be actuated by movement thereof in a direction substantially perpendicular to the direction of motion of the stylet (14). In an alternative embodiment, it is the catheter (43) which moves relative to the stylet (14).

20 Claims, 6 Drawing Sheets

(56) References Cited

U.S. PATENT DOCUMENTS

| | | |
|---|---|---|
| 2006/0224227 A1 | 10/2006 | Chobotov |
| 2007/0123971 A1* | 5/2007 | Kennedy et al. ............ 623/1.11 |
| 2007/0156224 A1* | 7/2007 | Cioanta et al. ............ 623/1.11 |
| 2007/0233222 A1* | 10/2007 | Roeder et al. ............ 623/1.11 |

FOREIGN PATENT DOCUMENTS

| | | |
|---|---|---|
| WO | WO 03/011185 A2 | 2/2003 |
| WO | WO 2007/064590 A | 6/2007 |
| WO | WO 2007/098232 A | 8/2007 |
| WO | WO 2009/011866 A | 1/2009 |

\* cited by examiner

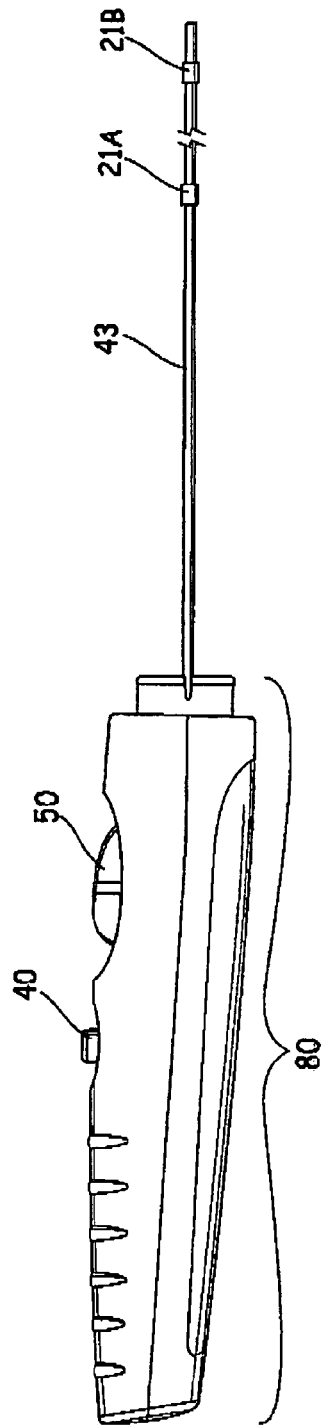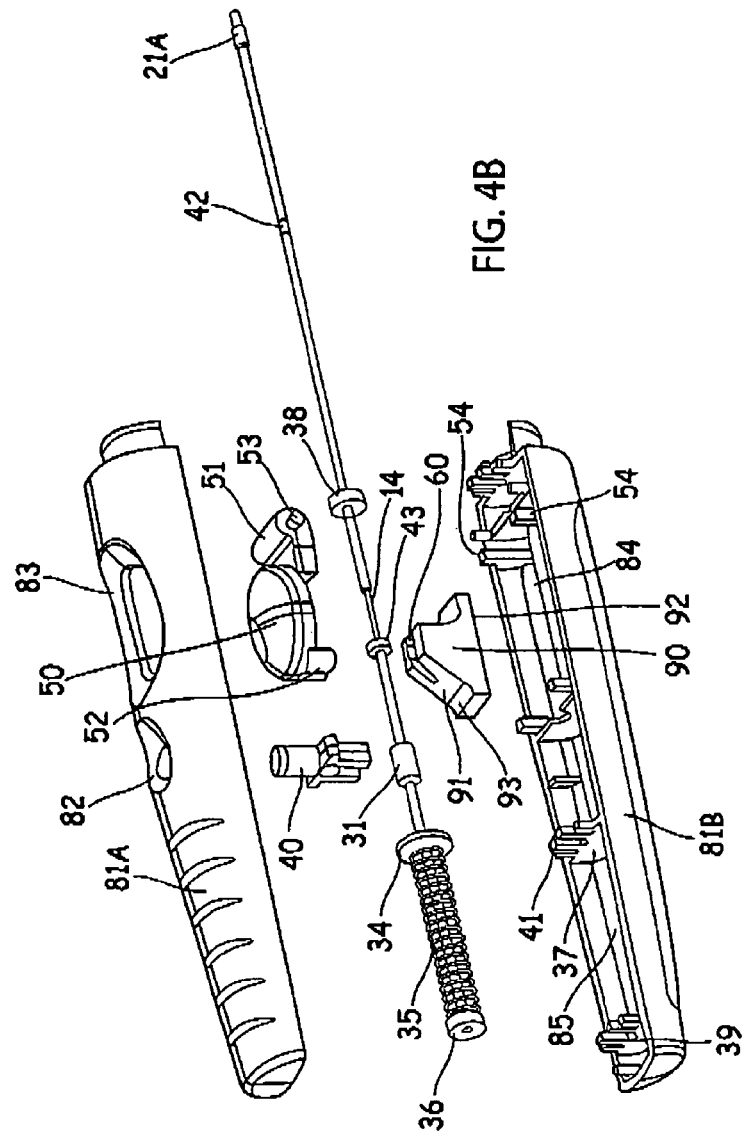

METHOD AND APPARATUS FOR INTRODUCING INTRALUMINAL PROSTHESES

CROSS-REFERENCE TO RELATED APPLICATIONS

This application claims priority of provisional application Ser. No. 61/004,804, filed Nov. 30, 2007.

TECHNICAL FIELD

The present invention relates to medical devices, in particular to an introducer assembly and to a method and apparatus for introducing a prosthesis or other implant into the vasculature of a patient.

BACKGROUND OF THE INVENTION

A variety of endoluminal introducer devices is known for deploying prostheses and other implants into the vasculature of a patient. One type of such introducers is designed to deploy a prosthesis or other implant for permanent implantation within a patient. Other types of introducer are designed both to deploy a prosthesis or other implant as well as to retrieve this on the completion of a particular medical procedure. One particular example of this latter type relates to the deployment and retrieval of filters within a body lumen of a patient. Introducers of this type, such as that disclosed in the Applicant's earlier United States patent application US-2005/0222604, includes a stylet provided with a hook at its distal end designed to hook into a loop provided on a filter. The stylet and filter are retained within a catheter during deployment and retrieval of the filter. The arrangement is such that the stylet can be pushed through its holding catheter so as to push the filter out of the distal end of the catheter, at which point the filter expands into its deployed configuration. The stylet can be unhooked from the filter to retain the filter in place during a medical procedure. The filter can be retrieved by hooking the stylet again into the loop of the filter and pulling this back into the holding catheter, upon which it collapses into a configuration analogous to that prior to its deployment.

In order to facilitate the deployment and retrieval operations, it is known for such filter introducer devices to be provided with a spring element, such as a coil spring, which biases the stylet to a retracted position within the holding catheter. An actuator, such as a button at a proximal end of the introducer, can be operated by a surgeon so as to push the stylet out of the holding catheter, against the force of the spring element. Release of the actuator causes the stylet to be pulled back into the catheter under the force of the spring element. Further details of an introducer of this nature are given below in the specific description, in connection with FIGS. 1 and 2.

The provision of a spring element biases the stylet into a retracted position, thus retaining the filter within the introducer device not only during the deployment/retrieval operations but also during transportation and other manipulation of the introducer.

A problem has been found to arise with introducers of the above nature, in that although the spring element normally effectively retains the filter or other device in the introducer, knocks or jolts to the introducer, which can occur particularly during transportation and other manipulation, have been known to cause the stylet to move longitudinally relative to the holding catheter to such an extent that the filter is pushed out of the catheter, unhooking itself from the stylet end and therefore coming loose from the introducer. When this occurs, the introducer assembly becomes unusable.

SUMMARY OF THE INVENTION

The present invention seeks to provide an improved introducer assembly, and an improved method and apparatus for introducing an intraluminal prosthesis or other device.

According to an aspect of the present invention, there is provided apparatus for introducing a device into a patient, including:

a catheter provided with a lumen therein;

a stylet located within the lumen of the catheter and moveable therealong, the stylet being provided with a coupling element at a distal end thereof;

a biasing element for biasing the stylet to a retracted position within the catheter;

an actuator for moving the stylet to an extended position against the force of the biasing element; and a locking device for locking the stylet relative to the catheter, wherein operation of the actuator requires unlocking of the locking device.

The preferred embodiment of introducer thus provides a locking device for locking the stylet in position, such that the stylet cannot move even against the force of the biasing element, until the locking device has been unlocked.

Preferably, the locking device includes a lock actuator co-operable with a receiver element on the stylet, wherein the lock actuator can lock to the receiver element in a plurality of positions on the receiver element. This provides for locking of the stylet relative to the catheter in a plurality of positions to accommodate, for example, different structures and dimensions of devices on the introducer. It can also allow in some embodiments for locking of the stylet and in particular the distal end thereof in a plurality of operating positions.

In the preferred embodiment, the lock actuator is moveable in a direction substantially perpendicular to the axis of the stylet. In practice, such an action requires a simple depression of a lock actuator button, as described below, in other words movement in a direction which will not effect longitudinal positioning of the introducer. This can substantially facilitate the medical procedure.

Advantageously, the introducer is provided with a handle including the actuator, the bias element and the lock actuator. Preferably, the actuator includes an actuator button acuatable by force substantially perpendicular to the axis of the stylet. Again, this allows a surgeon or other operator of the device to effect actuation of the stylet by a force substantially perpendicular to the axis of the introducer and thus by a force which allows more accurate positioning of the introducer within a patient. In this embodiment, there is preferably provided an actuator button co-operable with a carriage element connected to the stylet, which carriage element is moveable upon actuation of the actuation button. Advantageously, the carriage element includes a sloping surface for translating movement on the actuator button to a longitudinal movement of the carriage element and thereby of the stylet.

According to another aspect of the present invention, there is provided apparatus for introducing a device into a patient, including:

a catheter provided with a lumen therein;

a stylet located within the lumen of the catheter and moveable therealong, the stylet being provided with a coupling element at a distal end thereof;

a locking device for locking the stylet relative to the catheter, the locking device including a lock actuator and a receiver element located on one of the stylet and the catheter, wherein the lock actuator can engage a plurality of positions of the receiver element.

In one embodiment, the receiver element includes a plurality of discrete engagements members engageable with the lock actuator. In another embodiment, the receiving element is formed of a resilient material able to engage with the lock actuator in any position along the receiving element.

BRIEF DESCRIPTION OF THE DRAWINGS

Embodiments of the present invention are disclosed below, by way of example only, with reference to the accompanying drawings, in which:

FIG. 4A is a side elevational view of a handle assembly of the introducer of FIG. 3;

FIG. 4B is an exploded view of the handle assembly of FIG. 4A;

DESCRIPTION OF THE PREFERRED EMBODIMENTS OF THE INVENTION

Figure 1:
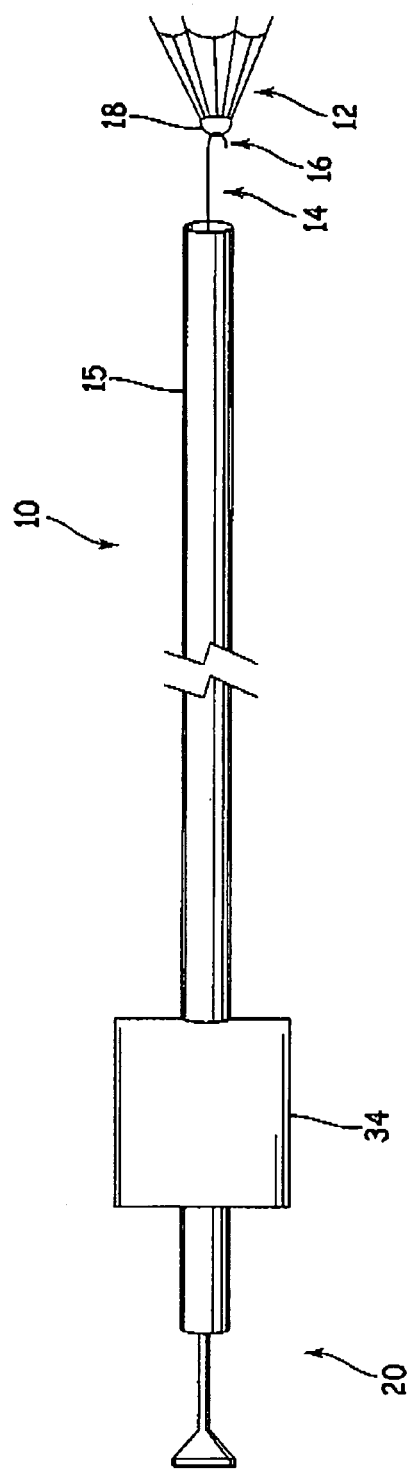
FIG. 1 is a schematic diagram of one example of prior art filter introducer assembly.

Referring to FIG. 1, there is shown an example of a prior art filter introducer system 10. The system is designed to deliver and deploy a filter 12 into a lumen of a patient, in this example through the jugular vein. The system 10 is also designed to retrieve the filter 12 at the end of a medical procedure. For this purpose, the introducer 10 is provided with a slidable stylet 14 housed within an introducer sheath 15, the end of which stylet 14 is provided with a hook 18 designed to hook onto a corresponding loop or ring 18 of the filter 12.

During deployment, the filter 12 is also located in the introducer sheath 15 and can be pushed out of this by a longitudinal movement of the stylet 14 in a deploying direction (that is, into the patient). Once the filter 12 has exited the sheath 15 and has been positioned as needed, the hook 16 can be manipulated as necessary so as to unhook this from the loop 18 of the filter. The introducer 10 can then be removed from the patient.

The filter 12 can be retrieved after the medical procedure by means of the same introducer 10. During such a retrieval procedure, the hook is advanced out of the sheath 15, hooked onto the loop 18 of the filter and retracted into the sheath 15. The retraction causes the filter 12 to collapse inwardly, in known manner.

It will be appreciated by the skilled person that in practice the introducer 10 is used through an outer sheath (not shown) which is pre-positioned into the patient's vasculature and used throughout the endoluminal medical procedure as a delivery channel, in accordance with well known procedures.

Figure 2:
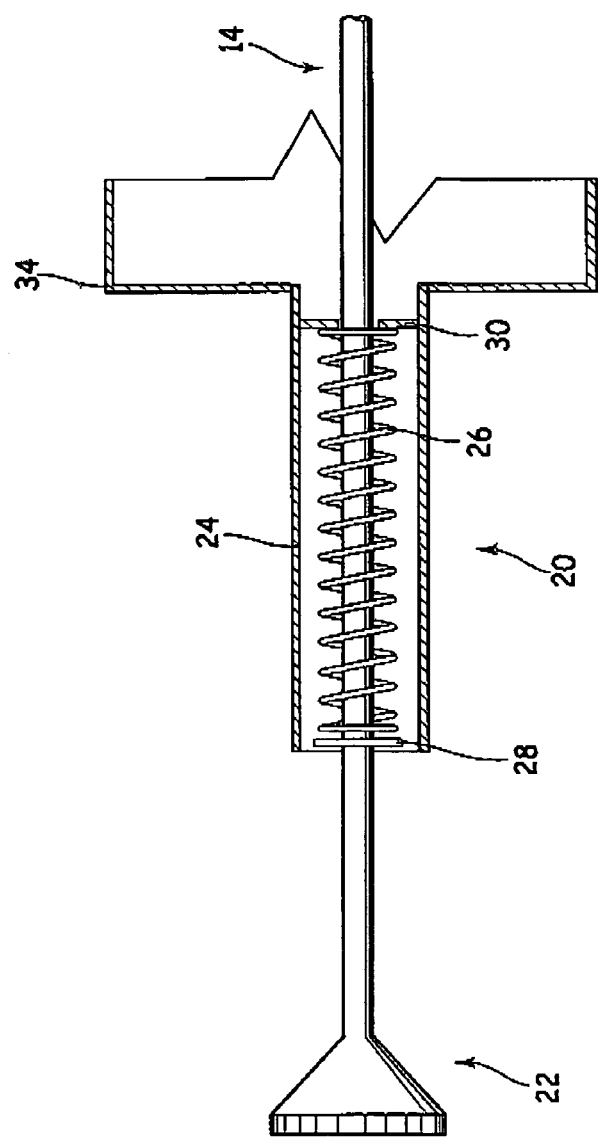
FIG. 2 is an enlarged view, in schematic form and in partial cross-section of a pusher unit of the introducer of FIG. 1.

In more specific detail, the stylet 14 is moved into and out of the introducer sheath 15 by means of a pusher member 20, shown in better detail in FIG. 2. The pusher member 20 includes an actuator in the form of a push button 22 connected to the proximal end of the stylet 14 and a housing element 24 within which there is located a coil spring 26 held between respective shoulders 28 and 30 attached to the stylet 14 and housing 24. The housing 24 couples to a valve and port assembly 34 of the introducer, the latter being well known in the art, for example of the conventional Y-type, and therefore not shown or described in detail herein.

Force applied on the pusher 22, typically by the surgeon's thumb, causes this to move towards the housing 24 and in so doing pushes the stylet 14 in a distal direction so as to push the hooked end 16 out of the introducer sheath 15. Thus, pushing the button 22 exposes the hook 16 to release the filter 12 during a filter deployment procedure or to grab a filter 12 fitted in a patient for retrieval thereof.

When the button 22 is pressed, the coil spring 26 becomes compressed by the two shoulders 28, 30. When the button 22 is released, the coil spring becomes free to extend again under its spring force, thereby pulling back the stylet 14 and hook 16. This feature has a number of primary functions. The first is to keep the filter in the introducer sheath 15 until the surgeon is ready to push this out for deployment, the action required to achieve this being a simple depression of the button 22 which the surgeon can perform with a thumb, for example. Another function is to provide for automatic withdrawal of the hook 16 back into the introducer sheath 15 once the filter 12 has been released, thus not requiring any other action by the surgeon apart from simple release of the button 22. Another function is to assist in the retrieval of the filter 12, whereupon release of the button 22 allows the spring 26 to pull the filter back into the introducer sheath 15.

The system of FIGS. 1 and 2 has proven simple and effective and is therefore widely used. However, it can suffer from a disadvantage in use. The assembly is typically supplied with the filter 12 in place in the introducer sheath, as with all such prosthesis and other implants, for sterilisation and other purposes. Under normal conditions, the coil spring 26 keeps the filter 12 housed in the introducer sheath 15 or other sheath of the device. However, this has been found not to be a secure system. In particular, it has been found that in some instances, for example during transportation and during manipulation of the assembly, the push button 22 can be inadvertently depressed, causing the filter 12 to be prematurely released from the introducer sheath. Should this occur, the filter 12 is wasted.

The present invention is directed to an improvement to the above described introducer assembly.

FIGS. 3 to 7 show a variety of embodiments of pusher unit suitable as replacements to the pusher unit 20 of the prior art example of introducer shown in FIGS. 1 and 2. Although the embodiments are described in connection with the deployment and retrieval of a filter, they are suitable for the deployment of a wide variety of prostheses and other implants, such as filters, occlusions devices, embolization coils, flow controllers, stents, stent grafts and many other endoluminally deployable devices.

Furthermore, although the preferred embodiments are described in connection with a stylet having a hooked end for coupling to the device to be deployed or retrieved, they are not limited to any particular device attachment mechanism. Just as one example, they can be used with a stylet provided with a looped end, such as a Gunther Tulip sold by the applicant.

The two primary embodiments discussed below are described in connection with introduction via the jugular vein and femoral artery respectively. It is to be understood that these are examples only for the purposes of this description and that the pusher systems taught herein can be used in any other endoluminal or percutaneous medical procedures.

Figure 3:
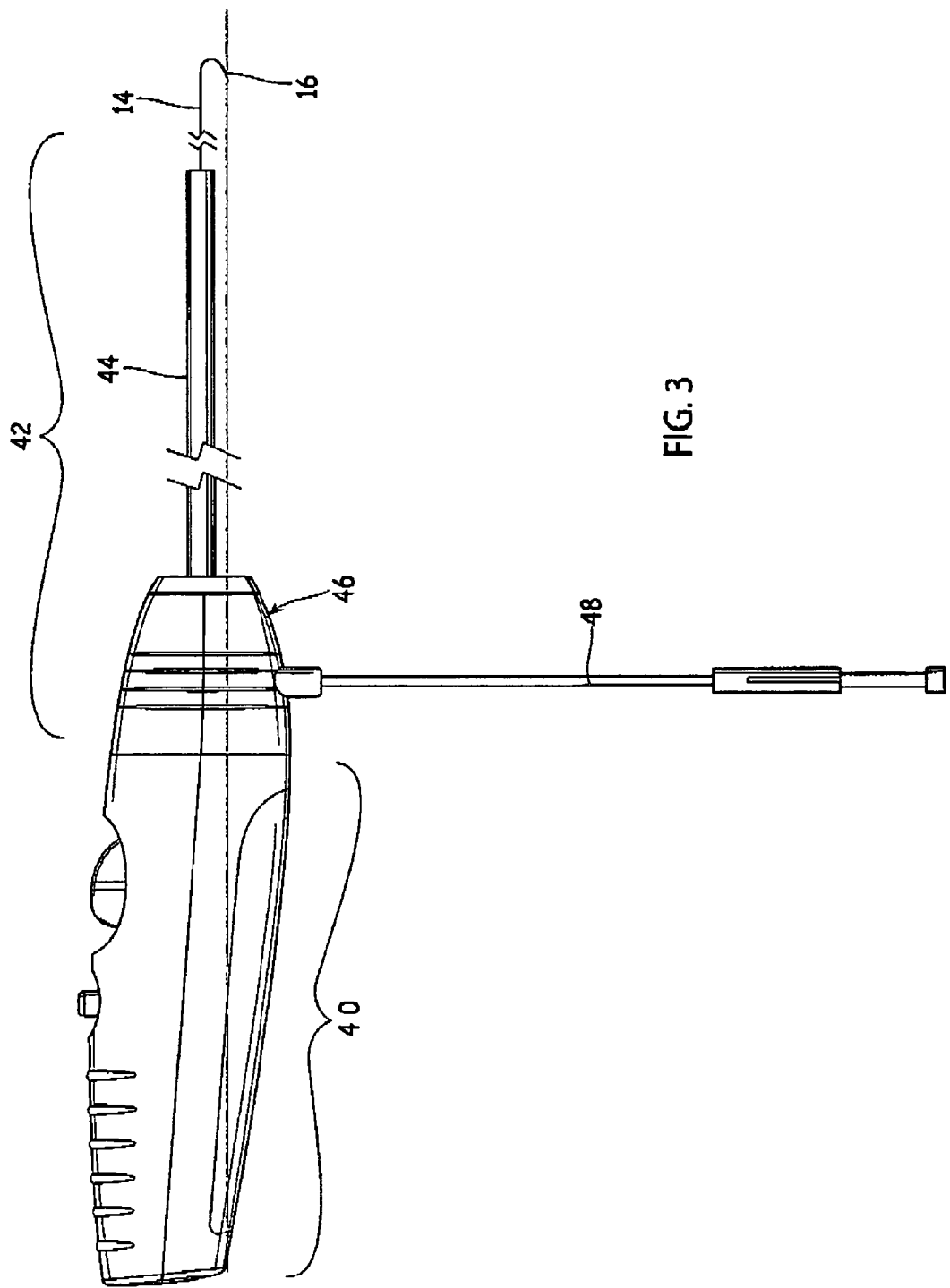
FIG. 3 is a side elevational view of a preferred embodiment of introducer and retrieval assembly according to the present invention.

Referring first to FIG. 3, there is shown one example of an entire introducer unit in accordance with the invention. The unit includes a handle 40, embodiments of which are described below, and an outer introducer section 42 which in this example includes an outer sheath 44, a handle/haemostatic valve and port unit 46 and an inlet/outlet tube 48 connectable to the interior of the outer sheath 44. Although the particular form of the outer introducer unit 42 is new, the components thereof are known in the art and therefore are not described in detail herein.

As with the prior art example shown in FIGS. 1 and 2, the assembly is provided with a stylus 14 having a hooked end 16 for attachment to a device. The stylus is coupled to the handle unit 40 for movement thereby to retract and extend the end 16, in a manner described below. The nature of the stylus 14 is not relevant to the present disclosure and may take other forms, such as having a looped end or of any other attachment end.

In some cases there may be provided additional units to the outer introducer assembly, such as additional valve and port assemblies for different medical uses. As units of this type are known in the art, they are not described herein.

Referring now to FIGS. 4A and 4B, there is shown a first embodiment of handle unit which in this description is used for the introduction of an inferior cava filter via the jugular vein. It will be appreciated, however, that the handle unit can be used the deployment and retrieval of any device which can be so deployed or retrieved via a catheter or sheath and is suitable for percutaneous or intraluminal insertion in a wide variety of locations of a patient.

A suitable inferior vena cava filter may comprise a hub at a proximal end thereof and a plurality of struts extending distally therefrom and provided with barbs at their respective distal ends for attachment to the vessel walls of a patient.

The handle 80 includes a long metal cannula 43 sufficiently flexible to provide the required trackability to the introducer but rigid enough to provide adequate pushability. Cannulae of such a type are known in the art.

FIG. 4A shows the embodiment of handle unit 80 and protruding cannula 43 in a side elevational view, while FIG. 4B shows the handle unit 80 in exploded form so as to display the internal components thereof.

The handle 80 is formed of an elongate casing formed in two halves 81a, 81b which engage along its length. The top half 81a is provided with two holes 82, 83 which allow access to an actuator or advancing button 50 and a locking button 41, both described in further detail below.

The handle also houses the proximal end of the cannula 43 within which is mounted the long flexible stylus 14.

An annular holding disc 38 is fixed to the proximal end of the cannula 43 and serves to fix the cannula 43 to the handle 80 in the longitudinal direction of the introducer. The stylus 14 is provided with a spring 35 over its proximal end, between two annular shoulder or stop discs 34, 36. The stop disc 36 is fixed to the proximal end of the stylus 14, while the stop disc 34 is slidable on the stylus 14. The interior of the handle 80 is provided with first and second walls 37, 39, delimiting the ends of a spring chamber 85 in the handle 80. The two stop members 34, 36 abut against the walls 37, 39. The distal wall 37 is provided with a slot or other aperture 41 therein allowing passage of the stylus 14.

The stylus 14 is also provided with an receiver or engagement element 31, described in full detail below, for use in locking the cannula 14.

At a location distal of the engagement element 31, there is provided a follower element 43 fixed to the stylus 14. The follower element 43 is designed so as to fit within a recess 60 of a carriage element 90. The carriage element 90 has, in this embodiment, a substantially flat lower surface 92 which is able to slide along a track 84 within the handle 80, such sliding movement causing, by virtue of the coupling of the handle element 90 to the follower element 43, the cannula 14 to slide with the carriage 90.

The advancing button 50 of the handle, shown in particular in FIG. 4b is provided with a hinge 51 having two opposing pins 53 upstanding therefrom, able to engage a suitable recess (not shown) in the top portion of the handle 80 and to rest upon supports 54 in the lower portion of the handle 80. The button 50 is also provided with a depending follower portion 52 which cooperates with a bevelled or sloping surface 91 of the carriage element 90. The design is such that upon pressure being applied to depress the button 50, this pivots about the hinge 51, causing the depending follower member 52 to rotate, to abut and then to slide along the sloping surface 91 of the carriage 90. As this occurs, the carriage 90 is moved in a distal direction, that is to the right in the view of FIG. 4b.

The proximal wall of the carriage unit 90, at the bottom end of the sloping surface 91, is provided with a recessed zone 93, in this embodiment in the form of a channel extending traverse to the direction of movement of the carriage. In operation, when the depending follower 52 reaches the end of the sloped surface 91, it suddenly falls into the recessed portion 93, providing an audible as well as a tactile jump in the movement of the button 50. This informs the surgeon that the button 50 has reached its fully depressed position and, in practice, that the stylus 14 is fully extended.

FIG. 4b also shows the locking button 40, which cooperates with the engagement element 31. Specific details of the locking button 40 are described in further detail below in connection with FIGS. 6a to 7b.

In operation of the handle 80, when the button 50 is depressed, the dependent element 52 slides down the sloping wall 91 and in so doing pushes the carriage 90 forwards, in a distal direction. The movement of the carriage 90, by virtue of the connection through the element 38, pushes the stylus 14 forwards as well as, in this example, the hooked end 16. When a filter or other device is hooked to the end of the stylus 14, this is in turn push out of its enveloping sheath, eventually allowing for release of the filter or other device carried by the introducer. As the carriage 90 and the proximal end 36 of the stylus 14 move forwards, the coil spring 35 is compressed by the end stop ring 36. Once the button 50 has been pushed all the way down, the surgeon feels and hears the click as the depending follower 52 drops into the channel 93.

As long as the button 50 is kept depressed and/or the locking button 40 is not engaged (as described below), when the button 50 is released, the compressed coil spring 35 can extend, thereby pulling the follower 90 backwards, which in turn pulls backwards the end 16 of the stylus 14, thereby retracting this. Such retraction is affected both for withdrawing the introducer after deployment of a filter or other device into a patient and also to pull into the introducer a filter or other device which is to be retrieved from a patient. Thus, the coil spring 35 is preferably of sufficient strength to be able to pull back and collapse a filter by the force of the spring alone.

Figures 5A, 5B:
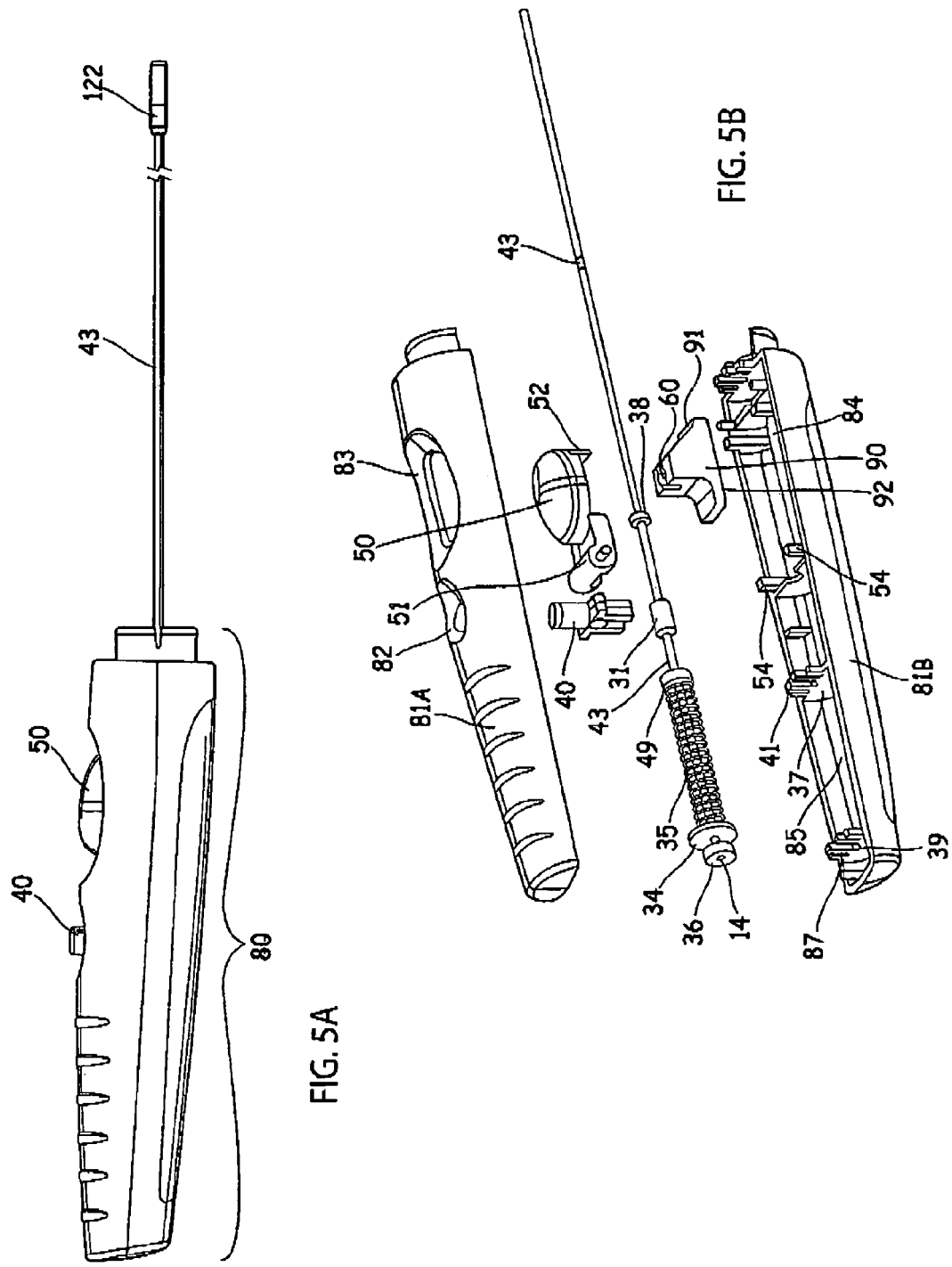
FIG. 5A is a side elevational view of another embodiment of handle assembly for the introducer of FIG. 3.
FIG. 5B is an exploded view of the handle assembly of FIG. 5A.

FIGS. 5a and 5b show another version of a handle having similar characteristics as the handle of FIGS. 4a and 4b. This handle has been designed to for an introducer suited for passage through the femoral artery. It will be appreciated, however, that the system could be used for any percutaneous or intraluminal insertion, not just through the femoral artery and can be used the deployment and retrieval of any device which can be so deployed or retrieved via a catheter or sheath.

In the embodiment of FIGS. 5a and 5b the mechanism could be said to be reversed compared to the embodiment of FIGS. 4a and 4b in that it operates to pull back the cannula 43, rather than to push forwards the stylus 14. In the embodiment of FIGS. 5a and 5b, the carriage element 90 is reversed compared to the embodiment of FIGS. 4a and 4b, as is the button 50, such that the carriage moves backwardly in a proximal direction upon depression of the button 50. The cannula 43 also extends to the proximal portion of the handle and is provided thereon with the engaging element 31 and with the spring retaining disc 49, which is fixed to the proximal end of the cannula end 43. The retaining disc or ring 36 is fixed to the end of the stylus 14 and a sliding disc 34 is located between the two fixing discs 36 and 43. The disc 36 at the end of the cannula 14 fits within a chamber 87 at the end of the handle 80 so as to fix the stylus 14 to the handle 80 such that the stylus 14 cannot move longitudinally relative to the handle. It is the cannula 43 which moves relative to the handle 80.

In a similar manner to the embodiment of FIGS. 4a and 4b, when the button 50 is depressed, leaving aside operation of the locking button 40, which will be described below, the dependent portion 52 of the button 50 slides down the sloping surface 91 of the carriage member 90, pushing the carriage member backwards in a proximal direction, thereby pulling the cannula 43 in a proximal direction so as to expose the end of the stylus 14. A device held by the stylus 14 can then be released or, in the case of a retrieval operation, cause the hook 16 of the stylus 14 to become uncovered so that it can grab on to an implanted device so as to effect its retrieval from within the patient.

As the carriage 90 moves the cannula 43 backwards, this compresses the spring 35 by means of the stop disc 49, the compression of a spring 35 being guided by the location of the distal end of the stylus 14 within the spring 35.

Thus, when the button 50 is released, leaving aside any operation of the locking button 40 which is described below, the spring 35 is able, by virtue of its spring force, to push the cannula 43 forwards, thereby to cause this to envelop again the end of the stylus 14. When the end 16 of the stylus 14 has caught a device to be retrieved, the spring 35 will cause that device, if of collapsible form, to be collapsed into the stylus 43 or, more particularly, an enveloping outer sheath, so as to capture the device within the introducer for withdrawal from the patient. In this regard, FIG. 5a shows the provision of a tubular receptacle 122 at the distal end of the cannula 43 for receiving a filter of other device.

FIGS. 6 and 7 show two examples of a preferred embodiment of locking member 40. It is preferred that the stylus 14/cannula 43 is kept locked longitudinally with respect to the handle 80 until the point that a surgeon desires to release or withdraw a device into or from a patient. In particular, it is preferred that the stylus and cannula are not movable relative to one another from the point of assembly of the introducer to the point at which it is to be used clinically, thus to be locked in particular during transportation and handling of the introducer assembly. The locking devices of FIGS. 6 and 7 provide such a function. The locking device 40 includes a button shank 141 the end of which is accessible from the aperture 82 in the handle 80. In this embodiment, the locking button includes first and second prong elements 142, 143 depending from the button shank 141 which in this embodiment are substantially parallel to one another.

The prongs 142, 143 are provided with internal surfaces having, in this embodiment, a plurality of vertically extending teeth 144, that is elongate teeth which extend in a direction substantially parallel to the direction of movement of the button 141.

Figure 6A:
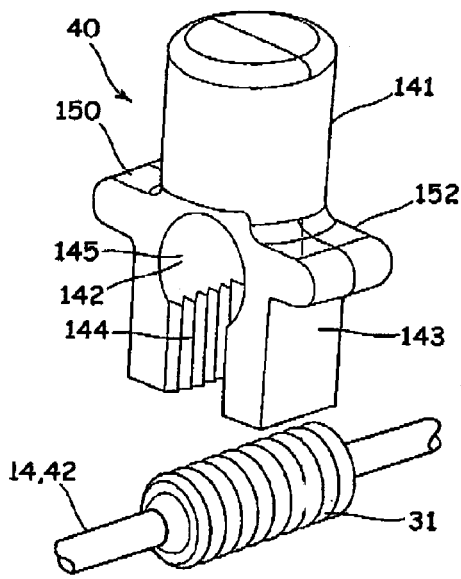
FIGS. 6A and 6B are schematic views of a first embodiment of locking assembly for the introducer of FIG. 3.
Figure 6B:
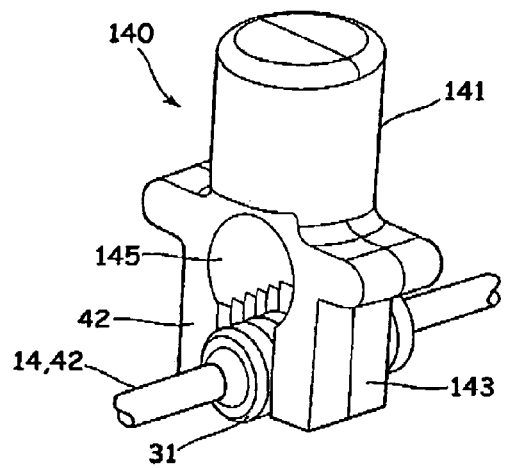
Figure 7A:
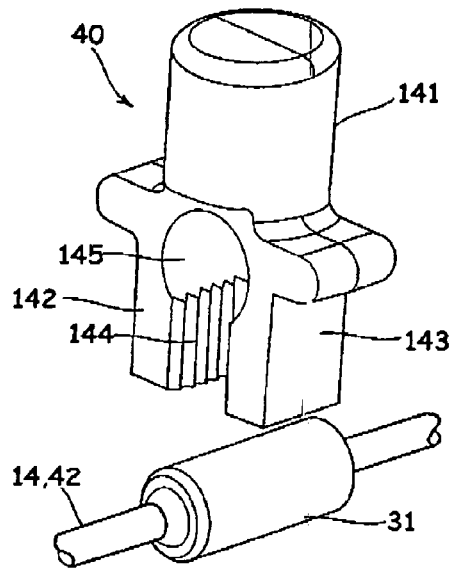
FIGS. 7A and 7B are schematic views of another embodiment of locking assembly for the introducer of FIG. 3.
Figure 7B:
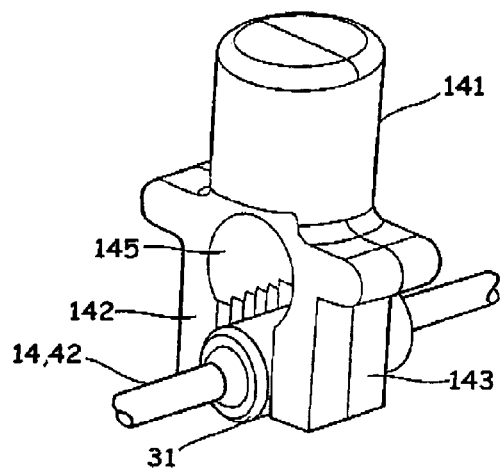

The engagement portion 31 provided on the stylus 14 or cannula 43, in the example of FIGS. 6a and 6b, is in the form of a grooved annular bushing, the grooves of which are sized and spaced to receive respective teeth 144 of the locking button 141. In the embodiment of FIGS. 7a and 7b, the engagement portion 31 is in the form of an elongate annular bushing made of resilient material, such as a suitable rubber or plastics material. It is such that the teeth 144 of the prongs 142, 143 can deform the surface of the bushing 31 so as to lock the bushing 31 in a longitudinal direction thereof when the teeth are engaged therewith. The bushing 31 could be of a form in which the deformation is resilient but it is not excluded that in some embodiments the teeth 144 could cut into the surface of the bushing 31.

As can be seen in FIGS. 6a to 7b, the locking button 141 is provided with an enlarged rounded aperture 145 above the pronged elements 142, 143 and in particular above the teeth 144. The enlarged aperture 145 is larger than the maximum diameter of the engagement element 31, such that when the button 141 is depressed to such an extent that the engagement portion 31 becomes located within the enlarged aperture 145, the engagement portion 31 can slide within the aperture 145, thus allowing for sliding of the stylus 14/cannula 43.

The button 141 is also provided with shoulders 150, 152 which abut suitable surfaces in the top half of the handle 80 so as to limit the upward movement of the button 141 within the handle 80. The lower surfaces of the prongs 142, 144 are, in this embodiment, substantially flat and in practice support one or more sprung elements (not shown) intended to bias the button upwardly, that is to extend of the aperture 82 when the button 141 is not depressed, up to the limit of the shoulders 150, 152 against suitable stop surfaces on the inside of the handle half 81A. The sprung element or elements thus retain the button normally in a upward-most position.

The arrangement is such that when the button 141 is in its uppermost position, the teeth 144 engage the grooves or surface of the engagement element 31, so as to lock the stylus 14 relative to the cannula 43. The button 141 must be depressed, so as to locate the engagement portion 31 in the enlarged aperture 145, before the stylus can be moved relative to the catheter or vice versa. Thus, a surgeon must first depress the locking button 40 to unlock the stylus/cannula and only then will the depression of the button 50 cause movement of the stylus/cannula so as to deploy the end of the stylus 14.

Thus, only when the button 40 is depressed can the end 16 of the stylus be exposed and there will be no movement of this even if the introducer unit is bashed during transportation or manipulation prior to its intended use.

The arrangement has another advantage, namely that the arrangement of locking device 40 and engagement element 31 are not dependent upon a particular longitudinal alignment of these two components. This allows not only for manufacturing tolerances but also the use of different sizes of devices to be deployed/retrieved. It allows the device to be locked in one of a plurality of relative positions of the cannula and stylus. For example, the end 16 of the stylus can be partially withdrawn and the entire unit locked by releasing the button 40, causing the teeth 144 to engage in the engagement element 31 at a different position of the latter. This allows partial withdrawal of the hooked end (in this embodiment). Similarly, it can, in the preferred embodiment, allow the surgeon to lock the stylus 14 in its most extended position, for example to assist in the retrieval of a filter or other device. Furthermore, in such a case, when the surgeon has determined that the device to be retrieved has been hooked on the end 16 of the stylus 14, simple depression of the locking button 40 will cause the handle 80 to come into action. It is preferred in some embodiments that this action is swift, which can facilitate in the collapse of the device being retrieved.

There are similar advantages during deployment, in providing for swift retraction of the hook end 16.

Although the above embodiments have been described with reference to the device being carried within the cannula 43, it will be appreciated that in some instances it is preferred to have a cannula 43 of a very small diameter, for example just slightly larger than the outer diameter of the stylus 14. In this case, the distal end of the introducer is provided within an enlarged portion 122, as shown in FIG. 5a for example, which is of a size sufficient to receive a device to be deployed or retrieved. In other embodiments, the device to be carried is held within the outer sheath 15.

As other aspects of the operation of the introducer device will be familiar to the person skilled in the art, such as the initial use of a guide wire, the fitting of an outer sheath, the flushing of the assembly with biocompatible solution, the location of the device by means of radiopaque markers and so on, these are not described in detail herein.

It will also be appreciated by the person skilled in the art that described above are specific practical examples embodying the principles of the invention taught herein and that modifications may be made thereto without departing from the scope of the teachings herein, which are to be limited solely by the scope of the appended claims and equivalents thereof.

What we claim is:

1. Apparatus for introducing a device into a patient, including:
   a catheter provided with a lumen therein;
   a stylet located within the lumen of the catheter and moveable therealong, the stylet being provided with a coupling element at a distal end thereof, the stylet defining a longitudinal axis;
   a biasing element for biasing the stylet to a retracted position within the catheter;
   an actuator for moving the stylet to an extended position against the force of the biasing element; and
   a locking device for locking the stylet and the catheter relative to one another, the locking device including a lock actuator, at least one engagement element, and a receiver element located on one of the stylet and the catheter, the lock actuator moveable in a direction toward and substantially perpendicular to the longitudinal axis of the stylet to unlock the stylet and the catheter relative to one another by disengaging the at least one engagement element from the receiver element;
   wherein operation of the actuator requires unlocking of the locking device.

2. Apparatus according to claim 1, wherein the lock actuator can lock to the receiver element in a plurality of positions on the receiver element.

3. Apparatus according to claim 2, wherein the actuator is configured to be activated by a force substantially perpendicular to the longitudinal axis of the stylet.

4. Apparatus according to claim 3, wherein the actuator includes an actuator button configured to receive the substantially perpendicular force.

5. Apparatus according to claim 2, wherein the introducer is provided with a handle including the actuator, the bias element and the lock actuator.

6. Apparatus according to claim 1, wherein the at least one engagement element comprises first and second facing engagement elements.

7. Apparatus according to claim 6, wherein each of the engagement elements is toothed.

8. Apparatus according to claim 7, wherein the receiving element includes a plurality of grooves for receiving teeth of the engagement elements.

9. Apparatus according to claim 8, wherein the grooves of the receiving element are in the form of axially spaced annular grooves.

10. Apparatus of claim 6, wherein the first and second engagement elements respectively engage opposing sides of the receiver element.

11. Apparatus according to claim 7, wherein the receiving element is formed of a resilient material able to engage with the lock actuator in any position along the receiving element.

12. Apparatus according to claim 1, wherein the actuator includes an actuator button co-operable with a carriage element connected to one of the stylet and the catheter, which carriage element is moveable upon actuation of the locking device.

13. Apparatus according to claim 12, wherein the carriage element includes a sloping surface for translating movement on the actuator to a longitudinal movement of the carriage element and thereby of the stylet.

14. Apparatus of claim 1, wherein the locking device is biased to a locked position.

15. Apparatus of claim 1, wherein the receiver element is located on the stylet.

16. Apparatus of claim 1, wherein the receiver element is located on the catheter.

17. Apparatus for introducing a device into a patient, including:
   a catheter provided with a lumen therein;
   a stylet located within the lumen of the catheter and moveable therealong, the stylet being provided with a coupling element at a distal end thereof, the stylet defining a longitudinal axis; and
   a locking device for locking the stylet relative to the catheter, the locking device including a lock actuator and a receiver element located on one of the stylet and the catheter, the lock actuator moveable in a direction toward and substantially perpendicular to the longitudinal axis of the stylet the stylet and the catheter relative to one another by disengaging the lock actuator from the receiver element;
   wherein the lock actuator can engage a plurality of positions of the receiver element.

18. Apparatus according to claim 17, wherein the receiver element includes a plurality of discrete engagements members engageable with the lock actuator.

19. Apparatus according to claim 17, wherein the receiving element is formed of a resilient material able to engage with the lock actuator in any position along the receiving element.

20. Apparatus for introducing a device into a patient, including:
   a catheter provided with a lumen therein;
   a stylet located within the lumen of the catheter and moveable therealong, the stylet being provided with a coupling element at a distal end thereof, the stylet defining a longitudinal axis;
   a biasing element for biasing the stylet to a retracted position within the catheter;
   an actuator for moving the stylet to an extended position against the force of the biasing element, the actuator being configured to be activated by a longitudinal force substantially perpendicular to the longitudinal axis of the stylet; and a locking device for locking the stylet and the catheter relative to one another, wherein operation of the actuator requires unlocking of the locking device and wherein the locking device includes a lock actuator co-operable with a receiver element on one of the stylet and the catheter, the lock actuator being able to lock to the receiver element in a plurality of positions on the receiver element; the locking device being moveable in a direction substantially perpendicular to the longitudinal axis of the stylet to lock the stylet and the catheter relative to one another.

* * * * *